United States Patent [19]

Brown et al.

[11] Patent Number: 5,336,614

[45] Date of Patent: Aug. 9, 1994

[54] SOFT AGAR ASSAY AND KIT

[75] Inventors: Ronald L. Brown, Rockville; Gretchen Schwartz, Wheaton, both of Md.

[73] Assignee: Quality Biological, Inc., Gaithersburg, Md.

[21] Appl. No.: 745,263

[22] Filed: Aug. 14, 1991

[51] Int. Cl.$^5$ ............................................... C12N 5/00
[52] U.S. Cl. ........................... 435/240.2; 435/240.1; 435/240.31; 435/810; 435/975
[58] Field of Search ............... 435/240.1, 240.3, 810, 435/975, 240.2, 240.31, 810, 975

[56] References Cited

U.S. PATENT DOCUMENTS

| | | | |
|---|---|---|---|
| 3,527,712 | 9/1970 | Renn et al. | 252/316 |
| 3,684,660 | 8/1972 | Kereluk et al. | 195/139 |
| 3,956,273 | 5/1976 | Guiseley | 260/209 |
| 4,089,748 | 5/1978 | Smernoff | 195/104 |
| 4,312,739 | 1/1982 | Hansson et al. | 204/299 |
| 4,411,990 | 10/1983 | Salmon et al. | 435/32 |
| 4,438,198 | 3/1984 | Schmer | 435/178 |
| 4,476,226 | 10/1984 | Hansen et al. | 435/299 |
| 4,572,897 | 2/1986 | Amotz et al. | 435/177 |
| 4,659,672 | 4/1987 | Provonchee et al. | 435/287 |
| 4,668,779 | 5/1987 | Brochon et al. | 536/121 |
| 4,952,686 | 8/1990 | Renn et al. | 536/114 |
| 4,963,489 | 10/1990 | Naughton et al. | 435/240.1 |
| 4,975,377 | 12/1990 | Key | 435/284 |

FOREIGN PATENT DOCUMENTS

| | | | |
|---|---|---|---|
| 0683727 | 9/1979 | European Pat. Off. | 435/240.1 |
| 8503520 | 8/1985 | World Int. Prop. O. | 435/252.1 |

OTHER PUBLICATIONS

Sing et al, Journal of Cellular Biochemistry, 39:107–115 (1989).
Pavlik et al, IN VITRO, vol. 19, No. 7, pp. 538–550 (1983).
Pavlik et al, The Journal of Urology, vol. 129, pp. 1254–1257 (1983).
Ichikawa et al, Proc. Natl. Acad. Sci., vol. 56, pp. 488–495 (1966).
Ihle et al, International Journal of Cell Cloning, 7:68–91 (1989).
Iscove, Methods for Serum-Free Culture of Neurophil and Lymphoid Cells, pp. 169–? (1984).
FMC BioProducts.
Dao et al, British Journal of Haematology, vol. 37, pp. 127–136 (1977).
Worton et al, J. Cell Physiol., vol. 74, pp. 171–182 (1969).
Coutinho et al, Blood, vol. 75, No. 11, pp. 2118–2129 (1990).
R. Ian Freshney, Alan R. Liss Inc., NY, 2nd Ed.; Culture of Animal Cells, Chapter 7, p. 62 (1987).
Culture of Animal Cells, Chapter 11, pp. 140–144 (1987).
Culture of Animal Cells, Chapter 23, pp. 333–334 (1987).

*Primary Examiner*—Douglas W. Robinson
*Assistant Examiner*—Deborah K. Ware
*Attorney, Agent, or Firm*—Birch, Stewart, Kolasch & Birch

[57] ABSTRACT

A kit and method for cultivating cells, particularly bone marrow cells, which utilizes a gel system having a gel strength low enough to allow the cells to settle into the gel during cultivation. The gel system is preferably formed from a mixture of methylcellulose and modified agarose.

12 Claims, 1 Drawing Sheet

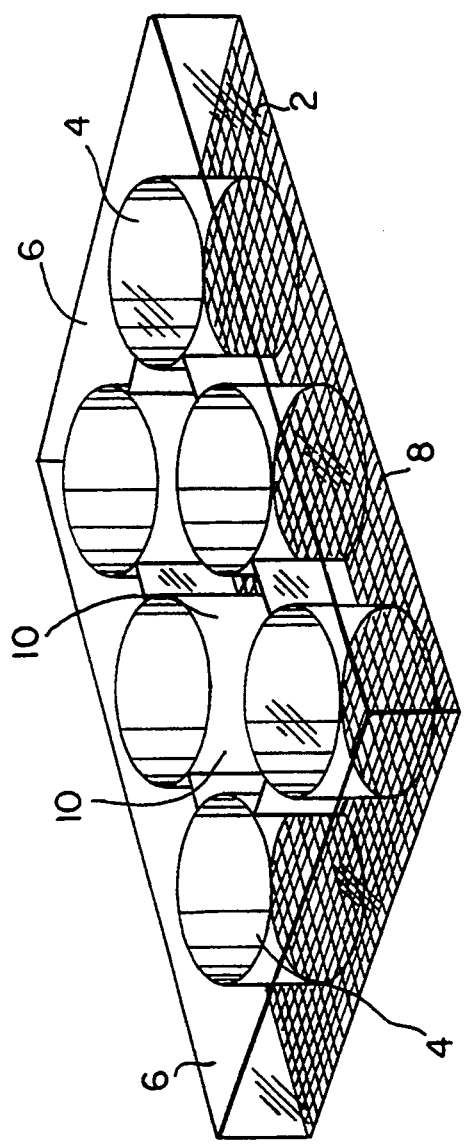

SOFT AGAR ASSAY AND KIT

BACKGROUND OF THE INVENTION

Typical soft agar assays consist of a gel matrix of either methylcellulose, agarose, agar or plasma clot mixed with basal medium, fetal bovine serum and, if necessary, growth factors. The preparation of this semi-solid matrix culture system is both laborious and time-consuming. Another disadvantage of these culture systems is that the cells to be cultured must be added to the gel when the gel is in a liquid form for proper growth of the cells. The addition of cells to either the methylcellulose or SeaPlaque ® alone, after it has formed a gel, does not support proliferation of the cells to form discrete colonies that can be quantitated to the extent necessary to run various biological tests, especially the soft agar assays.

SUMMARY OF THE INVENTION

The present invention provides a novel gel system which is particularly useful in supporting the growth of various types of cells, particularly eukaryotic cells such as human bone marrow cells, mouse bone marrow cells, etc. in vitro. One advantage of this gel system is that the gel can be prepared and formed into a layer and stored in a suitable container until it is needed for use. The cells to be cultivated are merely placed on top of the gel at room temperature. When the cells are incubated (usually at a temperature of about 37° C.), the cells will settle into the gel which provides a suitable environment for proliferation of the cells and formation of discrete colonies.

The gel system of the present invention has a gel strength at 4° C. (and preferably also at room temperature, i.e., 20°-22° C.) which is high enough so that the gel can be placed in a layer on the bottom of a container and can be handled and transported without disturbing the gel. At 37° C. the gel has a gel strength which is low enough to allow mammalian cells, particularly bone marrow cells, applied to the top surface thereof to settle into the gel in less than 24 hours. The gel is preferably formed from two different gel materials which each alone have different viscosity/temperature profiles.

The present invention is also directed to a kit for growing eukaryotic cells, particularly mammalian bone marrow cells, which comprises a container with the above-described solidified gel placed in the container. A preferred form of the kit comprises (a) a sterile container having (1) a transparent flat bottom surface with a grid thereon and (2) a side wall; and (b) a sterile solidified transparent or substantially transparent gel disposed in a substantially uniform gel layer having a thickness of 0.5 mm to 4 mm, preferably 1 mm to 3 mm on the bottom surface, the gel comprising modified agarose in a concentration of 1.75 to 7 mg/ml, preferably 2.6 to 4.4 mg/ml, most preferably 3.5 mg/ml; methylcellulose in a concentration of 6.5 to 26 mg/ml, preferably 9.8 to 16 mg/ml, most preferably 13 mg/ml; and an aqueous nutrient media containing nutrients necessary for growth of human or other species bone marrow cells.

The present invention is also directed to a method for growing mammalian cells which comprises applying the cells to a top surface of a gel having a gel strength which is low enough at 37° C. to allow the cells which are applied to the top surface of the gel to settle into the gel in less than 24 hours and incubating the cell containing gel matrix at 37° C. with 5% $CO_2$ and air in a fully humidified incubator. The cells will usually be incubated while they are settling into the gel matrix. The gel strength of the gel is preferably adjusted so that the cells are suspended within the gel matrix and do not settle to the bottom of the gel, i.e., the cells do not settle to the bottom surface of the well or container, during incubation at 37° C. Even after cultivation for 14 days, the bone marrow cells do not settle to the bottom of the gel.

The present invention is also directed to a method for preparing the above-described gel system and the novel gel system thus obtained. The gel system is preferably prepared by forming an aqueous solution of methylcellulose, forming an aqueous solution of modified agarose, mixing both of the aqueous solutions to form a gel system or mixture and allowing the resulting gel system to gel or set at a temperature below the gelling temperature of the gel system. The aqueous solution containing the modified agarose is preferably added to the aqueous solution containing methylcellulose and basal medium, etc. while vigorously mixing the solution, for example by vortexing or shaking. During this addition, the temperature of the solution is preferably maintained at a temperature above 20° C., preferably above 20° C. and less than 33° C. After all of the aqueous solution of modified agarose has been added to the aqueous solution of methylcellulose, the resulting solution is dispersed into a container, and the solution is allowed to cool to a temperature below the gel temperature of the gel system.

After the gel system has gelled or set, the kit is ready for use. The kit can be stored under refrigeration (usually at 4° C.). The cells to be cultivated are placed on the upper surface of the gel (usually in a small amount of an aqueous isotonic buffered solution or medium) and spread evenly over the surface of the gel. The kit is then placed in an incubator at 37° C. for cultivation of the cells. The cells will usually settle below the surface of the gel in less than 24 hours, depending upon the exact gel strength of the gel and the exact type of cells being cultivated.

BRIEF DESCRIPTION OF THE DRAWING

The sole drawing Figure is a perspective view of a container which can be used to prepare the kit of the present invention. It contains 6 (35 mm) wells that can be used for the assays.

DETAILED DESCRIPTION OF THE INVENTION

Various types of methylcellulose may be useful in accordance with the present invention. One type of methylcellulose which appears to be particularly useful is Methocell A4M Premium (Dow Chemical). The gelling properties of methylcellulose are inverse to those of agar, i.e., methylcellulose solutions of the A series gel at temperatures above 33° C. When solutions of A series methylcellulose are held at lower temperatures, the thixotropic properties of the methylcellulose result in a gel-like state at incubator temperature (33°-40° C. or 37° C.) if the fluid is not disturbed. This property may be important for preservation of colony morphology.

The solubility of methylcellulose is a function of the extent of methyl substitution achieved in manufacture. This varies from batch to batch and determines the concentration of undissolved fibers visible in the cultures. A batch of methylcellulose A4M with a low "fiber rating" can be specifically requested from Dow Chemical.

Other types of methylcellulose may also be useful. It is believed that preferred types of methylcellulose will be thixotropic, have a gel temperature at about the incubation temperature, i.e., about 33°–40° C., and form a gel-like state at 37° C. The methylcellulose will usually have a viscosity at 37° C. of 15 to 4,000 centipoise, preferably 3500 to 4500 centipoise.

A preferred type of agarose useful in accordance with the present invention is a modified agarose such as SeaPlaque ® which is a low gelling temperature agarose sold by FMC BioProducts. SeaPlaque ® agarose is prepared by the controlled introduction of hydroxyethyl groups into the agarose molecule. It is essentially neutral, both chemically and electrically. The reduction in gelling temperature of the agarose is a function of the degree of substitution by the hydroxyethylation, i.e., the more hydroxyethylation the lower the gelling temperature. One consequence of the hydroxyethylation of agarose is a reduction in gel strength. The reduction is related to the degree of substitution which is, in turn, reflected by changes in gelling temperature. A preferred gelling temperature of the modified agarose is 26° to 30° C. Additional information concerning preparation of modified agarose of this type can be found in U.S. Pat. No. 3,956,253 to Guiseley and which is hereby incorporated by reference.

The methylcellulose is preferably present in a greater amount than the modified agarose, agar or agarose. The weight ratio of the modified agarose, agar or agarose to methylcellulose is usually between 1:2 to 1:8, preferably 1:3 to 1:5. The optimum total concentration of the gel forming materials, i.e., modified agarose, agar, agarose and methylcellulose, in the gel system is 8.25 µg/ml to 33 mg/ml, preferably 10 to 21 mg/ml.

The kit has been used for the growth of bone marrow colonies consisting of granulocytes, monocytes and erythroid cells. The kit can be used to evaluate a subject's bone marrow cells for possible bone marrow transplantation. The cells of the bone marrow donor and/or recipient can be tested for their proliferative capacity. The kit can also be used in research. The kit can also be used to support the growth of mammalian cells equivalent to any other semi-solid matrix assay system, e.g., transformation assays and the like.

The nutrients and growth factors present in or added to the gel will be determined by the type of cells being cultivated and the purpose of the cultivation. The gel system of the present invention is particularly suitable for cultivation of anchorage independent cells. Exemplary cells which can be grown and the growth factors usually used in the cultivation of these cells include Eukaryotic cells—yeast, mammalian cells, such as human or mouse cells, vertebrate cell such as arian cells, etc.

Bone marrow cells—Mammalian bone marrow cells, particularly human and mouse bone marrow cells may be cultivated. These cells require cytokines as IL, GM-CSF, Erythropoietin, etc. for growth;

Peripheral blood colony forming cells—These cells also require the presence of cytokines for growth.

Growth factor-dependent cell lines—Cell lines which have been isolated from long-term bone marrow cultures and myeloid tumors using a growth factor such as interleukin 3 (IL-3). Examples of such cell lines are disclosed by Ihle et al, International Journal of Cell Cloning, 1:68-91 (1989), the entire contents of which is hereby incorporated by reference.

The growth factors present in the gel system could include Interleukin 1 through 11, fibroblast growth factor, platelet derived growth factor, epidermal growth factor, transforming growth factor (TGF) α or β, stem cell growth factor, cell-conditioned media (which contains many growth factors) or any other growth factor(s).

The container useful in accordance with the present invention preferably has a transparent flat bottom surface with a grid (for example, a 2 mm grid) formed on the underside of the bottom thereof. The container can be a multi-well container or a single-well container such as a Petri dish or the like. The gel, which is placed on the flat bottom surface, is preferably transparent or substantially transparent and is present as a substantially uniform layer on the bottom surface. In this way, the cells and cell colonies are readily visible and can be conveniently counted with respect to each unit area of the grid. The grid is preferably formed on the underside of the container and can be formed by scoring or painting. The grid can be formed when the plate is molded or stamped. In a preferred aspect, the grid is formed from one set of parallel raised transparent ridges which intersect at right angles with another set of raised parallel transparent ridges located on the underside of the transparent container.

After the container has been filled with the gel matrix, a cover can be placed on the container or the container can be wrapped with a sterile plastic sheet to maintain a sterile environment inside the wells of the container. The kit will preferably be sold with instructions for culturing a sample of cells.

As shown in the drawing Figure, the container of the present invention preferably comprises a lower member 2 having multiple wells 4 with flat bottom surfaces and side walls 6 around the periphery of the lower member. A grid 8 is provided on the bottom surface of the lower member 2. The gel is disposed in a layer on each of the flat bottom surfaces and a top member, e.g lid, may be provided which cooperates with the lower member to enclose the multiple wells. In order to maintain high humidity conditions in the container during cultivation of cells, the multiple wells can be disposed on a flat surface of the lower member with spaces 10 between the wells thereby providing a reservoir for sterile water which can be applied to the lower member, adjacent to the multiple wells. Such multi-well containers made from a transparent plastic material are commercially available.

EXAMPLE 1

Preparation of 2×IMDM

To the Iscove's Modified Dulbecco's Medium is added sodium bicarbonate (0.6%), Modified Eagles Medium Non-Essential Amino Acid Solution (200 µM), sodium pyruvate (2.0 mM), L-glutamine (4 mM) and antibiotics as required (in the following experiments Penicillin/Streptomycin (200 U/ml each)).

Preparation of 2.6% Methylcellulose in IMDM
(Mixture A)

5.2 g of methylcellulose (Dow Chemical, Methocel A4M Premium) are added to 100 ml of boiling sterile tissue culture grade water. Without further heating, the mixture is stirred continuously until the solution is a milky white suspension. The suspension is cooled to room temperature and 100 ml (equal volume) cold (4° C.) 2×Iscove's Modified Dulbecco's Medium (IMDM) is added while stirring. The solution is stirred at 4° C. for 24 to 48 hours. After this time the solution will be clear.

Preparation of 3.5% SeaPlaque®

3.5 g of SeaPlaque® is added to 100 ml of boiling tissue culture grade water with stirring. Once the SeaPlaque® is dissolved, the solution is allowed to cool to approximately 45° to 50° C. prior to mixing with methylcellulose.

Preparation of Serum Containing 1.3% Methylcellulose Solution (Mixture B)

To 25 ml of 2.6% methylcellulose (above), the following are added:
15 ml heat inactivated fetal bovine serum
5 ml, 10% deionized bovine serum albumin, fraction V
0.5 ml, $5 \times 10^{-3}$ M $\beta$-mercaptoethanol
0.5 ml L-asparagine stock solution (2 mg/ml)
0.25 ml, 7.5% sodium bicarbonate solution
0.5 ml 20 mM hemin (pH 7.5).

B. Preparation of Serum-Free 1.3% Methylcellulose Solution:

To 25 ml of the 2.6% methylcellulose in IMDM (above), the following are added:
10 ml deionized bovine serum albumin (100 mg/ml)
0.5 ml insulin (1 mg/ml)
0.5 ml cholesterol (10 mg/ml)
0.25 ml transferrin (80 mg/ml)
1.0 ml nucleosides (1 mg/ml):
2-deoxyadenosine
2-deoxycytidine
2-deoxyguanosine
2-deoxyuridine
0.5 ml $\beta$-mercaptoethanol ($5 \times 10^{-3}$M)
0.5 ml L-asparagine (2 mg/ml)
0.25 ml of 7.5% sodium bicarbonate
1.0 ml hemin (10 mM)
8.25 ml 1×IMDM The above mixture is stirred to insure mixing of all the components. After stirring, the mixture is allowed to set until all the bubbles disperse.

Preparation of the Gel System

To 45 ml of the medium containing methylcellulose, 5.0 ml of 3.5% SeaPlaque® is slowly added with repetitive pipetting and/or stirring. This solution is then aliquoted by needle and syringe or Eppendorf Sterile Combitips (Brinkman Instrument Co., Westbury, NY) into either 35 mM Petri dishes or 6-well plates (each with 2 mM grids) and allowed to gel at 4° C. for 1 hour.

EXAMPLE 2

Cell Growth Assays

Cells in 200–400 μl of an isotonic buffered solution were spread over the surface of the agar in each well tested. The cells (2 to $5 \times 10^4$ cells) were cultured for 14 days (human) or 7 days (mouse) at 37° C. in 5% $CO_2$ and air in a fully humidified atmosphere. After incubation, the number of colonies in each well were counted. When counting cells of erythroid lineage, a group of cells was considered to be a "colony" if it contained greater than 100 cells or 4 small colonies in close proximity consisting of 20–40 cells each. For granulocytes and monocytes, a group of cells was considered to be a "colony" if it contained greater than 50 cells.

The kits containing serum supported colony formation of human granulocytes, monocytes and erythroid precursors equivalent to or better than SeaPlaque® or methylcellulose alone (Table I).

TABLE I

Colony Formation in the Kits Versus Standard Assays per $10^5$ Cells.

| Assay: Serum Containing Medium | Species of Bone Marrow | [1]BFU-E Colony Number | [2]GM-Colony Number |
|---|---|---|---|
| Study I: | | | |
| Invention | Human | 294 | 59 |
| SeaPlaque | Human | 119 | 35 |
| Study II: | | | |
| Invention | Mouse | 45 | 39 |
| Methylcellulose | Mouse | 42 | 34 |
| Study III: | | | |
| Invention | Human | | 48 |
| SeaPlaque | Human | | 25 |

[1]BFU-E = Burst Forming Unit - Erythroid Colonies
[2]GM-Colony = Granulocyte/Monocyte Colonies The use of serum-free medium in the kit supported colony formation equivalent to serum-containing medium.

TABLE II

Murine GM-Colony Formation in the Invention with Serum Containing and Serum-Free Medium:

| | GM-Colony Number/$10^5$ cells | |
|---|---|---|
| Experiment | Serum | Serum-Free |
| Experiment I | 110 | 112 |
| Experiment II | 170 | 168 |

We claim:
1. A kit for growing eukaryotic cells, comprising:
a container; and
a solidified gel in said container which comprises modified agarose containing hydroxyethylated agarose in a concentration of 1.75 to 7 mg/ml and thixotropic methylcellulose which forms a gel at 33–40° C., wherein said thixotropic methylcellose is present in a concentration of 6.5 to 26 mg/ml, said gel having a gel strength at 37° C. which is low enough to allow eukaryotic cells applied to the upper surface thereof to settle below said upper surface of said gel, wherein eukaryotic cells applied to the top surface of the gel can be evenly spread over the surface of the gel.

2. The kit of claim 1, wherein said container has a transparent flat bottom surface with a grid and said gel is transparent and is present as a uniform layer on said bottom surface.

3. The kit of claim 1 which is wrapped in sterile plastic.

4. The kit of claim 1, wherein said gel is present in a layer and said layer of gel is 1 to 3 mm thick.

5. A kit for growing bone marrow cells, comprising:
(a) a sterile container having (1) a transparent flat bottom surface with a grid thereon and (2) a side wall; and
(b) a sterile solidified transparent gel disposed on said bottom surface in a single uniform layer having a thickness of 1 to 3 mm, said gel comprising modified agarose containing hydroxyethylated agarose, in a concentration of 1.75 to 7 mg/ml;

thixotropic methylcellulose which forms a gel at 33–40° C., in a concentration of 6.5 to 26 mg/ml; and an aqueous buffered solution having a pH of 6.9 to 7.4 containing nutrients necessary for growth of human bone marrow cells and having an osmolarity sufficient to maintain the integrity of the cells and allow the cells to proliferate, said gel having a gel strength at 37° C. which is low enough to allow bone marrow cells applied to the top surface of said layer to settle below said top surface of said layer in less than 24 hours without settling to the bottom of said gel.

6. A kit for growing bone marrow cells, comprising:
(a) a sterile container having (1) a transparent flat bottom surface and (2) a side wall; and
(b) a sterile solidified transparent gel disposed on said bottom surface in a single uniform layer having a thickness of 0.5 to 4 mm, said gel comprising modified agarose containing hydroxyethylated agarose, in a concentration of 1.75 to 7 mg/ml;

thixotropic methylcellulose which forms a gel at 33–40° C., in a concentration of 6.5 to 26 mg/ml; and an aqueous buffered solution containing nutrients necessary for growth of human bone marrow cells and having an osmolarity sufficient to maintain the integrity of the cells and allow the cells to proliferate, said gel having a gel strength at 37° C. which is low enough to allow bone marrow cells applied to the top surface of said layer to settle below said top surface of said layer in less than 24 hours.

7. A kit suitable for growing mammalian bone marrow cells, comprising:
a container having a bottom surface and side walls; and
a solidified gel in said container comprising (a) a first gel material selected from the group consisting of modified agarose, agar or agarose and (b) a second gel material which is thixotropic methylcellulose which forms a gel at 33–40° C., said gel having a gel strength at 37° C. which is low enough to allow said mammalian bone marrow cells applied to the upper surface thereof to settle below said upper surface of said gel within 24 hours, wherein mammalian bone marrow cells applied to the top surface of the gel can be evenly spread over the surface of the gel.

8. The kit of claim 7, wherein the total concentration of modified agarose, agar, agarose and methylcellulose is 10 to 21 mg/ml.

9. The kit of claim 7, wherein said first gel material has a lower gel temperature than said methylcellulose.

10. The kit of claim 7, wherein the gel temperature of said first gel material is 26° to 30° C.

11. The kit of claim 7, wherein said second gel material is modified agarose.

12. The kit of claim 7, wherein the weight ratio of said first gel material to said second gel material is between 1:3 to 1:5.

* * * * *

UNITED STATES PATENT AND TRADEMARK OFFICE
CERTIFICATE OF CORRECTION

PATENT NO. : 5,336,614
DATED : August 9, 1994
INVENTOR(S) : Brown et al.

It is certified that error appears in the above-identified patent and that said Letters Patent is hereby corrected as shown below:

Column 1, after the title, insert
--This invention was made with U.S. Federal Government support under Contract No. DK 42753-01 awarded by the National Institute of Diabetes and Digestive and Kidney Disease. The Government has certain rights in the invention.--

Signed and Sealed this

Sixth Day of April, 1999

Attest:

Attesting Officer

Q. TODD DICKINSON

Acting Commissioner of Patents and Trademarks